(12) United States Patent
Thorn

(10) Patent No.: US 8,224,419 B2
(45) Date of Patent: Jul. 17, 2012

(54) MEDICAL VISUALIZATION METHOD, COMBINED DISPLAY/INPUT DEVICE, AND COMPUTER PROGRAM PRODUCT

(75) Inventor: Matthias Thorn, Möhrendorf (DE)

(73) Assignee: Siemens Aktiengesellschaft, Munich (DE)

( * ) Notice: Subject to any disclaimer, the term of this patent is extended or adjusted under 35 U.S.C. 154(b) by 825 days.

(21) Appl. No.: 11/677,148

(22) Filed: Feb. 21, 2007

(65) Prior Publication Data

US 2007/0238960 A1 Oct. 11, 2007

(30) Foreign Application Priority Data

Feb. 23, 2006 (DE) .......................... 10 2006 008 508

(51) Int. Cl.
*A61B 5/05* (2006.01)
(52) U.S. Cl. ......... 600/407; 600/436; 128/922; 709/223
(58) Field of Classification Search .................. 600/407, 600/436; 128/922; 709/223
See application file for complete search history.

(56) References Cited

U.S. PATENT DOCUMENTS

| | | | |
|---|---|---|---|
| 5,803,914 A | | 9/1998 | Ryals et al. |
| 6,760,767 B1 * | | 7/2004 | Miesbauer et al. ........... 709/227 |
| 6,876,759 B2 * | | 4/2005 | Keller et al. ................... 382/128 |
| 2002/0054038 A1 | | 5/2002 | Nemoto |
| 2003/0028543 A1 * | | 2/2003 | Dusberger ..................... 707/100 |
| 2005/0148861 A1 * | | 7/2005 | Ramanathan et al. ........ 600/410 |
| 2005/0246366 A1 | | 11/2005 | Kouchi et al. |
| 2008/0071895 A1 * | | 3/2008 | Johnson et al. ............... 709/223 |

FOREIGN PATENT DOCUMENTS

| | | |
|---|---|---|
| CA | 2 178 774 | 11/2003 |
| DE | 102 55 958 A1 | 6/2004 |
| EP | 1 416 420 A1 | 5/2004 |
| EP | 1 704 816 A2 | 9/2006 |
| WO | WO 02/31642 | 4/2002 |
| WO | WO 2005/031650 | 4/2005 |

\* cited by examiner

*Primary Examiner* — Brian Casler
*Assistant Examiner* — Joseph M Santos
(74) *Attorney, Agent, or Firm* — Schiff Hardin LLP

(57) ABSTRACT

In a medical visualization method, wherein: a series of organ slice images are acquired at different points in time by an imaging modality; the acquired organ slice images are stored in an image data memory with information about the series and/or the point in time of the acquisition. A data connection between an input/output device and the image data memory is established and the available series are determined. Series that are specific to the organ are symbolically represented with a display of the availability thereof. The organ slice images associated with a selected series are displayed. An input/output device as well as a computer program product operates according to the method.

15 Claims, 1 Drawing Sheet

MEDICAL VISUALIZATION METHOD, COMBINED DISPLAY/INPUT DEVICE, AND COMPUTER PROGRAM PRODUCT

BACKGROUND OF THE INVENTION

1. Field of the Invention

The present invention concerns a medical visualization method for selection and display of organ slice images acquired by means of an imaging modality. The invention furthermore concerns a combined display/input device suitable for implementation of the visualization method as well as a corresponding computer program product.

2. Description of the Prior Art

For an oncological or cardiological diagnosis, it is typical to use a series of organ slice images generated by means of imaging modalities. For example, computed tomography or x-ray tomography are suitable for use as imaging modalities. Magnetic resonance tomography, positron emission tomography as well as ultrasound are also suitable for acquisition of such organ slice images.

For oncological or cardiological questions it is furthermore required to be able to observe organs in the context of blood circulation or in a movement cycle at various phases. For example, certain conditions of a heart can be observed only at a certain point in time of the heartbeat cycle; they are not visible at other points in time. A suitable contrast agent can be introduced into the bloodstream of a patient to increase the contrast for observation of the organs by means of an imaging modality. The injected contrast agent bolus reaches the organ to be observed (for example a liver) at a defined point in time via the blood circulation. Upon passage of the contrast agent bolus through the organ, various flow or movement stages of the organ can thus be observed in succession. A liver tumor can be visible in a flow phase and invisible in another flow phase.

A series of organ slice images of the organ to be examined is therefore acquired with the images respectively being acquired at different points in time for a medical diagnosis. For examination and for diagnosis of a heart it is typical to acquire a series of organ slice images dependent on the ECG signal and, after these acquisitions, to respectively reconstruct the heart from the acquired series at specific phases of the heartbeat cycle. These phases are measured, for example, in a percent of a complete heartbeat cycle. Series in intervals of 5 or 10% of a heartbeat cycle are typical. As a result, the cardiologist can select from 10 to 20 series of organ slices, each series representing a given point in time of the heartbeat cycle.

For the observation of the liver, it is typical to use the various flow phases for designation of the acquired series of organ slice images. The flow characteristic of a liver is thus commonly sub-divided into three to five phases, namely into native, arterial and venous, and additionally into portal venous and late venous.

The viewer (for example a radiologist) considers the different phases of the organ to be examined, or the acquired organ slice images associated with those phases, in order to be make to pose a targeted diagnosis. For this purpose, he or she compares the organ slice images in the various phases with one another in order, for example, to be able to differentiate a tumor from a pseudo-lesion.

It is known to prepare organ slice images in the background, or to load organ slice images from an image data memory while the viewer considers the organ slice images that have already been loaded. In order to achieve a safer diagnosis, the viewer must consider all organ slice images, which occupies a great deal of time.

Furthermore, for a given patient it is known to load all acquired organ slice images from an image data memory and to provide them for selection in a menu.

SUMMARY OF THE INVENTION

An object of the present invention is to provide a visualization method of the aforementioned type which is user-friendly and enables a rapid navigation between the series of organ slice images with regard to a reliable diagnosis. Furthermore, it is an object of the invention to provide a display/input device as well as a corresponding computer program product suitable for the implementation of the visualization method.

The first object is achieved in accordance with the invention by a medical visualization method, wherein: a series of organ slice images are acquired at different points in time by an imaging modality; the acquired organ slice images are stored in an image data memory with information about the series and/or the point in time of the acquisition, a data connection between an input/output device and the image data storage is established, the available series are determined, series that are specific to the organ are symbolically represented with display of the respective availability, and the organ slice images associated with a selected series are displayed.

The invention is based on the recognition that the viewer must jump back and forth between the different points in time or phases to produce a reliable diagnosis. The suitable series can then be taken from a comparison of the organ slice images of various series. In order to enable this, the acquired organ slice images are stored in an image data memory with information about the series and/or the point in time of the acquisition. In this manner it is possible to associate the organ slice images with the respective series. In order to be able to switch between the individual series, a symbolic representation of all series provided specific to the organ ensues with simultaneous indication of the respective availability of the series. Through the association of the organ slice images with the respective series it is namely possible to establish whether individual series are not available at all. The viewer thus recognizes at a glance which series are available and can quickly switch back and forth between the available series. By consideration of relatively fewer organ slice images of different series it is thus possible for the user to quickly arrive at the organ slice image suitable for the diagnosis, or to quickly derive the correct diagnosis from the organ slice images of the various series.

In other words, by the symbolic display that the viewer learns, for example, that ten phases of a heartbeat cycle would generally be presentable, but of these ten phases only five are available for the selected patient since organ slice images were only acquired only for these phases. For the comparison of organ slice images of the identical body position but from different series, upon changing the series the user does not have to work through the entire image material in order to arrive at the comparable body position; rather the viewer can arrive directly at this position by direct selection of the series.

Whether a data connection with an external or an internal image data storage is established to check the availability thereby plays no rile for the invention. If, for example, the organ slice images are stored on a medical imaging apparatus or, respectively, on its image data storage, these organ slice images can be accessed, for example, via a network. On the other hand, the data sets with regard to the organ slice images can also have been transferred via the network or via data media to an internal data storage of the input/output device. It can likewise be imagined that the organ slice images are stored on a central patient databank which can in turn be accessed via a network or a direct data connection line.

In an embodiment, the data connection and the presence of organ slice images of a series are checked to establish the available series; given lack of the data connection a temporary unavailability of a series is concluded and given absence of organ slice images of a series a general unavailability of the series is concluded and the information about a temporary or general unavailability of a series are symbolically displayed.

By this procedure the viewer learns that a series of organ slice images were, for example, acquired and stored for a selected patient, but is temporarily not available (for example due to an interrupted network connection or a transfer error). This information is significant since the viewer is informed that he or she can still access further image material for the ultimate diagnosis. Since no organ slice images for a series are available since the image data memory is not present, the viewer does not need to take this series into consideration to generate the diagnosis.

In a further embodiment, a currently executed selection of a series is also symbolically displayed. The viewer thus learns which series he or she has already considered. Duplicate considerations are reduced only to those that are necessary.

A pre-selection of a series is appropriately set, and this pre-selection with regard to a series is symbolically indicated. The pre-selection can be fixed or can be set by the viewer. The display of the pre-selection gives the viewer the possibility to initially consider the organ slice images of the pre-selected series for generation of his diagnosis, such that the organ slice image suitable for the diagnosis can be quickly located with a significant time savings that is not to be underestimated.

In principle, a number of different symbols or shapes can be selected for the symbolic representation of the described information. For example, a specific symbol can be associated with each specific item of information. The selected symbols can be, for example, simple graphical elements with different structures. It is also possible to use as symbols graphical elements that have a design that allows the type of the displayed information to be intuitively concluded. For clarity, however, it is advantageous to use color codes, patterns and/or alphanumerical characters for the symbolic representation. Such elements can be shown in common in a simple manner, such that the function of the provision of quick information is ensured. For example, the availability of a series or its consideration status can be coded via a suitable color code in a simple manner. This can likewise be effected by various selected patterns.

The series are appropriately symbolically represented by alphanumerical characters, the availability by a color coding, and the consideration status as well as the pre-selection by a colored corner, a colored point or a colored border of different colors. The predetermined series for an implemented organ examination can be displayed next to one another in the form of rectangles or squares that are respectively provided with an alphanumerical character characterizing the respective series. The availability or the consideration status can be indicated by filling of the respective square or rectangle with a correspondingly provided color. This type of the representation also allows further information to be displayed, for example by a colored border respectively surrounding the square or the rectangle of a series, or can be represented by colored corners or colored points implemented in the squares or rectangles. A display requiring a small space requirement is achieved in this manner that quickly provides the viewer with the information necessary to him or her in a useful manner. In other words, with a glance at a corresponding display, the viewer can read off the necessary information.

Since a selection by the viewer for visualization of the organ slice images of individual series is made by a suitable input, information arises that is likewise suitable for symbolic representation. Here it is necessary to store the information generated during the usage. This information is appropriately stored as belonging to the stored organ slice images or in a header of the corresponding files of the organ slice images. In the first case the data storage of the input/output device is itself used while in the other case the information is directly stored in the organ slice images already present for a patient. The latter offers the elegance that existing user information, together with the acquisition information, is respectively associated with the specific organ slice image of a patient. In the first case, this association must be stored via a saved link in order to be able to be re-associated with a respective organ slice image or a respective series given a later use.

The second of the above object is achieved in accordance with the invention by a combined input/output device which has an input device, a display device, an internal or external data storage, a data connection line that can be connected with the image data storage, an interface for connection with a medical image acquisition apparatus, and a computer for implementation of the visualization method described above.

The combined display/input device can be either a free-standing device such as, for example, a workstation or a PC that is, for example, connected via a network with a centrally-archived image data storage or an image acquisition apparatus, to it can be part of an image acquisition apparatus itself, whereby the image data memory is directly accessed. For implementation of the method it is required that the acquired organ slice images are respectively stored with the information about the series and/or the point in time of the acquisition.

The last of the above objects is achieved in accordance with the invention by a computer program product that generates the visualization method upon execution thereof on a computer. The computer program product enables the program-controlled workflow of the visualization method, including the acquisition of the organ slice images. Alternatively, it is also possible for the computer program product to evaluate organ slice images stored with the corresponding information and enable the symbolic representation for selection by a viewer.

DESCRIPTION OF THE PREFERRED EMBODIMENTS

Figure 1:
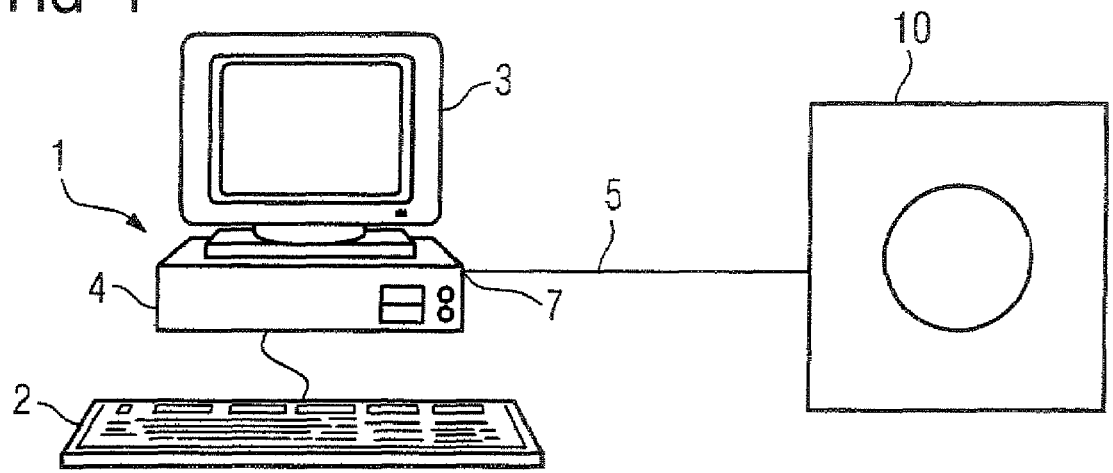
FIG. 1 shows a combined display/input device in accordance with the invention for visualization of organ slice images stored in series.

A combined display/input device 1 for visualization of acquired organ slice images is schematically shown in FIG. 1. The display/input device 1 has an input device 2 such as, for example, a computer keyboard, and a display device 3 in the form of a high-resolution monitor. For controlling the visualization method, the display/input device 1 has a computer 4 that is connected via a data connection line 5 with an image acquisition apparatus 10. The data connection line 5 is suitable both for access to organ slice images stored in the image acquisition apparatus 10 and for controlling the image acquisition apparatus 10 for acquisition of desired organ slice images. A connection 7 fashioned as a suitable interface is provided.

In order to enable the diagnosis of an organ (such as, for example, a liver or a heart), a series of organ slice images is acquired with the image acquisition apparatus 10 activated at various points in time, starting from a contrast agent administration. The image acquisition apparatus 10 is, for example, a computed tomography apparatus. The respective organ slice images associated with a corresponding phase or series are stored in an image data storage of the image acquisition apparatus 10 with the information about their point in time or series type.

For visualization of the organ slice images, this information with regard to the availability of a series examination subject is evaluated in the input/output device via the data connection line 5. For example, this occurs after selection of a specific patient, with the input/output device 1 being caused to search for corresponding stored organ slice images. For this purpose, the check of organ slice images available for a series is possible by the association of the information of the point in time or the type of the series.

For overview of the available series (for example for heart acquisitions), series at 5, 10, 15, 20% etc. of a heartbeat cycle are symbolically represented on the display device 3, with the series that are actually available for the patient being made recognizable by a color code. If, for example, only series at 10, 30 and 80% of a heartbeat cycle are present, the symbols representing the series thus receive a different color than those of the unavailable series.

Furthermore, a pre-selection of a series presumably suitable for diagnosis as well as an only temporary unavailability are displayed as additional information. Further information for a symbolic display is evaluated during usage. For example, an already-considered series is made recognizable by a corresponding color border or a corresponding colored corner or by another symbol. This display allows the user to make a quick navigation through the organ slice images that are present for the respective patient, such that the organ slice images suitable for the diagnosis can be located quickly.

Figure 2:
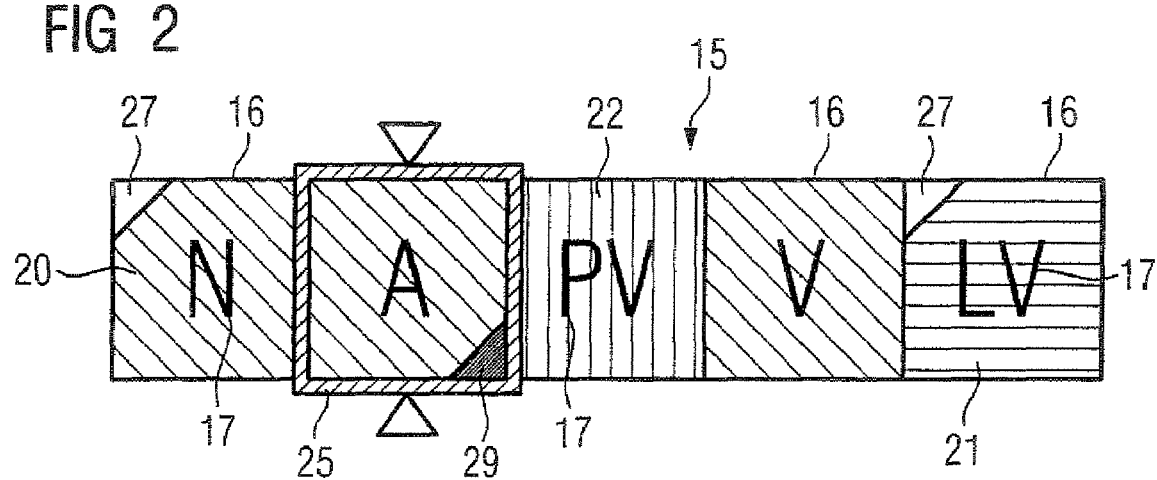
FIG. 2 is an exemplary symbolic representation for visualization of organ slice images of a liver in accordance with the invention.

Such a symbolic representation is exemplarily shown in FIG. 2 for diagnosis of a liver tumor. The symbol display 15 generated on the display device 3 for this purpose has a total of 5 boxes 16 that are respectively labeled with alphanumerical characters. Each box 16, corresponding to its alphanumerical character 17, corresponds to a flow phase necessary for diagnosis of the liver. "N" thus stands for the native flow phase, "A" for the arterial, "PV" for the portal venous, "V" for the venous and "LV" for the late venous. The stored organ slice images are characterized corresponding to these flow phases or are associated with these phases.

For a quick navigation through the organ slice images, each box 16 is additionally highlighted with a color/pattern code 20, 21, 22. The flow phases N, A and V thus exhibit a different color code 20 than the flow phases PV and LV. The shown color/pattern codes 20, 21, 22 can be represented on a color monitor by different colors. The selected color/pattern code 20 means that the flow phases N, A and V are available. According to the color/pattern code 22, the flow phase PV is in fact available in principle, but can temporarily not be selected since, for example, a data transfer error exists. The color/pattern code 21 of the flow phase LV symbolizes the fact that no organ slice images are available for this series for the selected patients.

Furthermore, the information that the organ slice images of the flow phase A are currently visualized is indicated by a border 25 that can additionally also contain a color code. Furthermore, a consideration status is shown by the colored corner 27. The setting of a colored corner 27 in a box 16 of a flow phase means that the correspondingly identified series was not yet considered. A further colored corner 29 (for example black) at the right lower corner of the box 16 it indicates that this series of a flow phase is set as a pre-selection.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for visualizing medical images of an organ for which a plurality of image series of the organ are commonly acquired, as commonly-acquired image series, said method comprising:

operating an imaging system to acquire multiple series of organ slice images of said organ, with each slice image in each slice series being acquired at a different point in time, with at least some of said multiple series respectively corresponding to at least some of said commonly-acquired image series;

storing and sorting said slice images of said organ in a memory and associating information in said memory with each slice image therein, and selecting said information from the group consisting of a designation of the point in time at which the slice image associated with the information was acquired, and a designation of the series, among said multiple series, of which the slice image associated with the information is a member;

establishing a data connection between an input/output device and said memory;

via said input/output device, making a pre-selection from among said plurality of commonly-acquired image series, as a pre-selected series;

via said input/output device, automatically determining which of said commonly-acquired image series is currently available for display at said input/output device, due to (1) being among the multiple series in said memory, and (2) being able to be correctly transmitted to the input/output device from the memory via the data connection, with all of said commonly-acquired series that satisfy (1) and (2) being determined by said input/output device as being an available series, and any of said commonly-acquired series for which either (1) or (2) is not satisfied being determined by said input/output device as an unavailable series;

when said pre-selected series is among said available series, displaying the pre-selected series at a display screen of said input/output device together with others among said available series, and together with a representation of each commonly-acquired series that is an unavailable series, each of said pre-selected series and said others of said available series, and each representation of an unavailable series, being shown at said display screen with a symbolism having a symbolism characteristic that can have a plurality of different visual appearances;

showing said pre-selected series and said others of said available series at said display screen, as active series, with said symbolism having a first of said different visual appearances;

showing any of said representations of unavailable series at said display screen with said symbolism having a second of said different visual appearances when the commercially-acquired series indicated by the representation thereof is unavailable due to not satisfying (1); and showing any of said representations of unavailable series at said display screen with said symbolism having a third of said different visual appearances when the commonly-acquired series indicated by the representation thereof is unavailable due to not satisfying (2).

2. A method as claimed in claim 1 comprising selecting said symbolism from the group consisting of color codes, patterns and alpha-numeric characters.

3. A method as claimed in claim 1 wherein said symbolism is a first symbolism and wherein said pre-selected series is a currently selected series, and comprising, at said display screen, showing any of said active series and any of said representations of unavailable series, that was previously selected as a pre-selected series prior to said currently selected series, with a second symbolism that has a symbolism characteristic that can have a plurality of different visual appearances.

4. A method as claimed in claim 3 comprising selecting said second symbolism from the group consisting of color codes, patterns and alpha-numeric characters.

5. A method as claimed in claim 1 comprising indicating said preselected series at said display screen with a marker, that is different from said symbolism.

6. A method as claimed in claim 5 comprising selecting said marker from the group consisting of a colored corner, a colored point, and a colored border.

7. A method as claimed in claim 1 comprising generating an electronic file for the multiple series of organ slice images, and storing, in a header of said electronic file, header information including a designation of said symbolism.

8. A computerized device for visualizing medical images, comprising:

a memory containing slice images of an organ acquired from an imaging modality in multiple series, with each slice image in each slice series being acquired at a different point in time, with at least some of said multiple series respectively corresponding to at least some of said commonly-acquired image series;

said slice images of said organ in said memory being associated with information in said memory, said information being selected from the group consisting of a designation of the point in time at which the slice image associated with the information was acquired, and a designation of the series, among said multiple series, of which the slice image associated with the information is a member;

an input/output device comprising a display screen;

a data connection between said input/output device and said memory;

said input/output device being configured to allow a user to make a pre-selection from among said plurality of commonly-acquired image series, as a pre-selected series;

said input/output device being configured to automatically determine which of said commonly-acquired image series is currently available for display at said input/output device, due to (1) being among the multiple series in said memory, and (2) being able to be correctly transmitted to the input/output device from the memory via the data connection, with all of said commonly-acquired series that satisfy (1) and (2) being determined by said input/output device as being an available series, and any of said commonly-acquired series for which either (1) or (2) is not satisfied being determined by said input/output device as an unavailable series;

when said pre-selected series is among said available series, said input/output device being configured to display the pre-selected series at said display screen together with others among said available series, and together with a representation of each commonly-acquired series that is an unavailable series, each of said pre-selected series and said others of said available series, and each representation of an unavailable series, being shown at said display screen with a symbolism having a symbolism characteristic that can have a plurality of different visual appearances;

said input/output device being configured to show said pre-selected series and said others of said available series at said display screen, as active series, with said symbolism having a first of said different visual appearances;

said input/output device being configured to show any of said representations of unavailable series at said display screen with said symbolism having a second of said different visual appearances when the commercially-acquired series indicated by the representation thereof is unavailable due to not satisfying (1); and said input/output device being configured to show any of said representations of unavailable series at said display screen with said symbolism having a third of said different visual appearances when the commonly-acquired series indicated by the representation thereof is unavailable due to not satisfying (2).

9. A computerized device as claimed in claim 8 wherein said input/output device is configured to use, as said symbolism, a symbolism selected from the group consisting of color codes, patterns and alpha-numeric characters.

10. A computerized device as claimed in claim 8 wherein said symbolism is a first symbolism and wherein said pre-selected series is a currently selected series, and wherein said input/output device is configured to show, at said display screen, any of said active series and any of said representations of unavailable series, that was previously selected as a pre-selected series prior to said currently selected series, with a second symbolism that has a symbolism characteristic that can have a plurality of different visual appearances.

11. A computerized device as claimed in claim 10 wherein said input/out device is configured to use, as said second symbolism, a symbolism selected from the group consisting of color codes, patterns and alpha-numeric characters.

12. A computerized device as claimed in claim 8 wherein said input/output device is configured to indicate said preselected series at said display screen with a marker, that is different from said symbolism.

13. A computerized device as claimed in claim 8 wherein said input/output device is configured to use, as said marker, a marker selected from the group consisting of a colored corner, a colored point, and a colored border.

14. A computerized device as claimed in claim 8 wherein said input/output device is configured to generate an electronic file for the multiple series of organ slice images, and to store header information, in a header of said electronic file, including a designation of said symbolism.

15. A non-transitory, computer-readable storage medium encoded with programming instructions for visualizing medical images of an organ, for which a plurality of image series of the organ are commonly acquired, as commonly-acquired images series, said storage medium being loadable into an input/output device of an imaging system that includes an imaging modality that acquires multiple slices of organ slice images of said organ, with each slice image in each slice series being acquired at a different point in time, at least some of said multiple series respectively corresponding to at least some of said commonly-acquired image series, and that includes a memory in which said slice images of said organ are sorted and stored and respectively associated with information in said memory, said information being selected from the group consisting of a designation of the point in time at which the slice image associated with the information was acquired, and a designation of the series, among said multiple series, of which the slice image associated with the information is a member, said programming instructions causing said input/output device to:

establish a data connection between an input/output device and said memory;

via said input/output device, make a pre-selection from among said plurality of commonly-acquired image series, as a pre-selected series;

via said input/output device, automatically determine which of said commonly-acquired image series is currently available for display at said input/output device, due to (1) being among the multiple series in said memory, and (2) being able to be correctly transmitted to the input/output device from the memory via the data connection, with all of said commonly-acquired series that satisfy (1) and (2) being determined by said input/output device as being an available series, and any of said commonly-acquired series for which either (1) or (2) is not satisfied being determined by said input/output device as an unavailable series;

when said pre-selected series is among said available series, display the pre-selected series at a display screen of said input/output device together with others among said available series, and together with a representation of each commonly-acquired series that is an unavailable series, and to cause each of said pre-selected series and said others of said available series, and each representation of an unavailable series, to be shown at said display screen with a symbolism having a symbolism characteristic that can have a plurality of different visual appearances;

show said pre-selected series and said others of said available series at said display screen, as active series, with said symbolism having a first of said different visual appearances;

show any of said representations of unavailable series at said display screen with said symbolism having a second of said different visual appearances when the commercially-acquired series indicated by the representation thereof is unavailable due to not satisfying (1); and show any of said representations of unavailable series at said display screen with said symbolism having a third of said different visual appearances when the commonly-acquired series indicated by the representation thereof is unavailable due to not satisfying (2).

\* \* \* \* \*